United States Patent [19]
Nakanishi et al.

[11] Patent Number: 5,201,727
[45] Date of Patent: Apr. 13, 1993

[54] ABSORBENT ARTICLE

[75] Inventors: Hirofumi Nakanishi, Ichikai; Hiromi Baba; Akira Sakurai, both of Utsunomiya, all of Japan

[73] Assignee: Kao Corporation, Tokyo, Japan

[21] Appl. No.: 762,434

[22] Filed: Sep. 19, 1991

[30] Foreign Application Priority Data

Sep. 27, 1990 [JP] Japan .................................. 2-258154
Jun. 28, 1991 [JP] Japan .................................. 3-159028

[51] Int. Cl.⁵ ...................... A61F 13/15; A61F 13/20
[52] U.S. Cl. .................................... 604/390; 604/358; 604/385.1; 604/386; 604/387; 604/389
[58] Field of Search ............... 604/389, 390, 386, 387, 604/358, 385.1

[56] References Cited
U.S. PATENT DOCUMENTS

| | | |
|---|---|---|
| 4,589,876 | 5/1986 | Van Tilburg . |
| 4,687,478 | 8/1987 | Van Tilburg ........................ 604/387 |
| 4,701,178 | 10/1987 | Glaug et al. ......................... 604/387 |
| 4,773,905 | 9/1988 | Molee et al. . |
| 4,813,947 | 3/1989 | Korpman ............................ 604/390 |
| 4,900,320 | 2/1990 | McCoy ................................ 604/387 |
| 4,936,839 | 6/1990 | Molee et al. . |
| 4,985,025 | 1/1991 | Lingertat et al. ................... 604/390 |

FOREIGN PATENT DOCUMENTS

| | | |
|---|---|---|
| 3326026 | 2/1985 | Fed. Rep. of Germany ...... 604/389 |
| 60-75058 | 4/1985 | Japan . |
| 1-111002 | 4/1989 | Japan . |
| 213455 | 1/1990 | Japan . |

Primary Examiner—Randall L. Green
Assistant Examiner—Paul Zuttarelli
Attorney, Agent, or Firm—Birch, Stewart, Kolasch & Birch

[57] ABSTRACT

An absorbent article including a liquid permeable outer material, a liquid impermeable antileakage material, and a liquid retentive absorbent element interposed therebetween, and formed in a generally vertically elongated shape, the improvement including a pair of fixing elements extending outwardly in a width direction from both longitudinal edges of the absorbent article, each of the fixing element being provided on at least a back side thereof with a first adhesive portion having no separate paper, the pair of fixing elements being able to be adhered to and separated from a back side of the absorbent article through the first adhesive portions.

4 Claims, 6 Drawing Sheets

ABSORBENT ARTICLE

BACKGROUND OF THE INVENTION

1. Field of the Invention

This invention relates to an absorbent article such as, catamenial napkin, incontinent pad, catamenial pad, etc. which its wearer wears together with an undergarment (hereinafter represented by "shorts") in the narrow crotch, and more particularly to an absorbent article having a high antileakage property.

2. Description of the Prior Art

The conventional absorbent article such as a catamenial napkin basically includes a liquid permeable outer material, a liquid impermeable antileakage material, and a liquid retentive absorbent element interposed therebetween. In recent years, by developing and introducing a new material such as an absorbent polymer for the absorbent element in place of the conventional cotton-like pulp or absorbent paper, an attempt has been made to improve the absorption ability of the absorbent article. Another attempt has been made in which a liquid permeable sheet is given a liquid permeability by forming tiny perforations on a hydrophobic sheet and is placed next to a non-woven fabric as a conventional fiber aggregate. This combination is used as an outer material in order to improve the absorption ability of the absorbent article.

However, even in an absorbent article in which a new material is introduced and in which each component element has an excellent efficiency, sideward leakage still occurs frequently in actual use. For example, in a case of catamenial napkins, blood leaks sidewardly and the blood reaches the shorts, creating inconvenience for the wearer and raising doubts about whether or not the original efficiency of the absorbent article is fully exhibited. The main causes of leakage in a catamenial napkin, which occur irrespective of the original efficiency of each component element, as mentioned above, are as follows:

(1) When a wearer fixes a catamenial napkin on shorts, the position of the catamenial napkin is one-sided either rightward or leftward at the crotch portion of the shorts and there exists a part of the crotch portion which is not covered with the catamenial napkin from the begining.

(2) Even if a wearer successfully correctly fixes a catamenial napkin, i.e., in a generally center area of the shorts without being one-sided either rightward or leftward relative to the crotch portion, the catamenial napkin is frequently twisted and deformed into a rolled-up state wherein each longitudinal edge of the catamenial napkin is overlapped with the central portion because of the wearer's physical activity or movements, and an edge portion of the crotch portion which was covered with the catamenial napkin right after it was fixed is exposed due to the rolled-up deformation.

(3) When a wearer moves, it is impossible to firmly fix a catamenial napkin to the crotch portion of shorts only by fixing means such as the adhesive which a catamenial napkin usually has, and the catamenial napkin is displaced from a predetermined position and exposes the crotch portion.

Leakage caused by the above (1) through (3) is also greatly affected by the shorts to be worn by a wearer. For example, particularly when the width of the crotch portion is wide compared with the width of the napkin, or when fit to the wearer's body is bad and loosened, leakage tends to occur comparatively easily.

Therefore, in order to solve these problems, many proposals have been made in which an absorbent article is provided with a pair of flexible flaps each extending in the width direction away from a central portion of each longitudinal edge of the absorbent article (Japanese Patent Early Laid-open Publication Nos. Sho 60-75058, Hei 1-111002, Hei 2-13455, etc.). In the case of these absorbent articles, the crotch portion of the shorts, when in use, is sandwiched between and fixed by the flaps in order to stabilize the absorbent article in the shorts, thereby improving the antileakage property.

For example, a sanitary napkin described in Japanese Patent Early Laid-open Publication No. Sho 60-75058 is designed such that in a central position of each vertical side of an absorbent article, a flexible flap formed of liquid permeable outer material and liquid impermeable antileakage material extends from each side of an absorbent element, so that the flap, in use, can be pulled out from the edge portion of the shorts and fixed to an outer side of the shorts by fixing and connecting means disposed on a rear surface of the flap, thereby stabilizing the sanitary napkin and improving the antileakage property. In this sanitary napkin, it is important, in order to have it exhibit its full antileakage property, to form an antileakage wall by placing the absorbent element in such a manner as that both sides of the absorbent element face upward when the shorts are worn. If the shorts are worn in such a state as just mentioned, leakage can be prevented to some extent. However, the following problems arise.

① Action for pulling out the flaps from both ends of the crotch of the shorts is not necessarily stable; the sanitary napkin cannot be worn together with the shorts in a constant state; and the sanitary napkin is sometimes twisted into an irregular form from the beginning of its use to thereby cause leakage.

② If the width of the crotch portion of the shorts is wider than the width of the absorbent element, it becomes difficult to fix the sanitary napkin itself to the shorts or otherwise it sometimes happens that the sanitary napkin cannot be firmly secured to the crotch portion because an outwardly-bent area of the crotch portion is reduced.

③ Even if the antileakage wall portion is successfully formed at each side of the absorbent element by firmly securing the pair of flaps in ②, it sometimes happens that the antileakage wall portion is twisted toward and contacted with the outer surface of the absorbent element to stain the flaps themselves with blood because the width of the antileakage wall portion of the flap is wide. Therefore, although staining of the shorts can be prevented by the flaps to some extent, it sometimes happens that the flaps themselves are stained while the wearer is moving or acting and the inner crotch portion is stained with blood by the stained flaps. This sometimes provides even greater inconvenience to the wearer.

In any case, when the conventional absorbent articles described in the above-mentioned Publications are correctly fixed to a right position of shorts, leakage mentioned in the above (1) through (3) can be prevented to some extent, but in the case of shorts having a poor fit to the wearer's body and shorts having a crotch portion which is wider in width than the width of an absorbent element, the flaps fully cover the outer surface of the absorbent article. As a result, leakage cannot necessarily be prevented effectively and the flaps are stained which, in turn, stains the inner crotch portion with blood, etc. through the stained flaps.

SUMMARY OF THE INVENTION

An object of the present invention is to provide an absorbent article which can, easily and without fail, be fixed to undergarments such as shorts irrespective of the shape of the undergarments and fit to a wearer's body, and which is barely twisted even if the wearer performs physical activity, and which can maintain an initial wearing state stably from the beginning to the end of the use, and which can prevent leakage (particularly, sideward leakage) effectively, and which requires no release paper and is easy to handle.

Inventors of the present invention found that the above object can be achieved by providing certain fixing means to the absorbent articles so as to be used for fixing to the undergarments.

The present invention has been made on a basis of the above finding and provides an absorbent article including a liquid permeable outer material, a liquid impermeable antileakage material, and a liquid retentive absorbent element interposed therebetween, and formed in a generally vertically elongated shape, the improvement including a pair of fixing elements extending outwardly in a width direction from both longitudinal edges of said absorbent article, each of said fixing element being provided on at least a back side thereof with a first adhesive portion having no release paper, said pair of fixing elements being able to be adhered to and separated from a back side of said absorbent article through said first adhesive portions.

According to the absorbent article of the present invention, after the absorbent article is brought into contact with an inner surface of a crotch portion of shorts in a state where the fixing elements are spread in the width direction of the absorbent article, the fixing elements are bent into their initial states and the first adhesive portions thereof are adhered to an outer surface of the crotch portion in such a manner that both the side edges of the crotch portion are wrapped up with the fixing elements to fix the absorbent article to the shorts. If the shorts are worn in the foregoing state, the liquid permeable portion is located in a body fluids discharge portion and therefore, even if the wearer performs physical activity, after the shorts are worn, the fixing elements are never tucked up; the crotch portion is normally wrapped up by the fixing elements in a state where the fixing elements are adhered to the crotch portion through the first adhesive portions; and the absorbent article can be stably held in the initial state from the beginning to the end of the use.

Accordingly, an absorbent article of the present invention can, easily and without fail, be fixed to undergarments such as shorts irrespective of the shape of the undergarments and fit to a wearer's body; it is barely twisted even if the wearer performs physical activity; it can maintain an initial wearing state stably from the beginning to the end of the use; it can prevent leakage (particularly, sideward leakage) effectively; and it requires no release paper and is easy to handle.

BRIEF DESCRIPTION OF THE DRAWINGS

FIG. 7(c) is a view, corresponding to FIG. 9(b), of a partly modified embodiment of the sixth embodiment.

DETAILED DESCRIPTION OF THE EMBODIMENT

The present invention will be described hereinafter with reference to the embodiments shown in FIGS. 1(a) through 10.

Figure 1A:
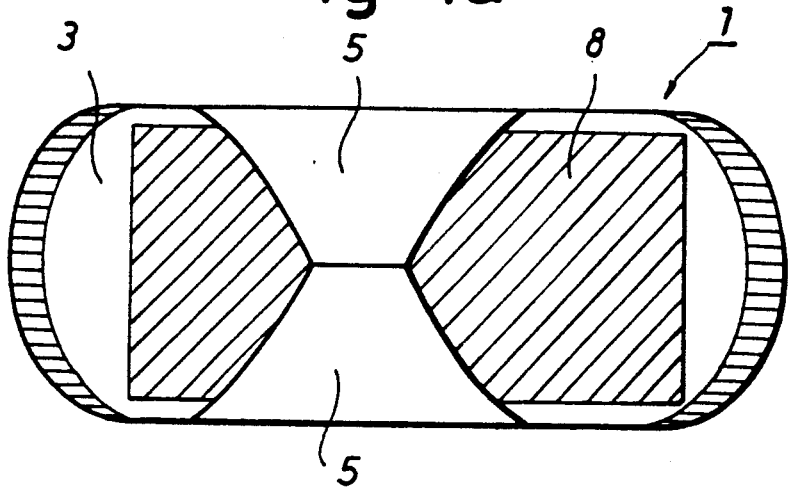
FIG. 1(a) is a plan view showing a back side of a first embodiment of the present invention.
Figure 1B:
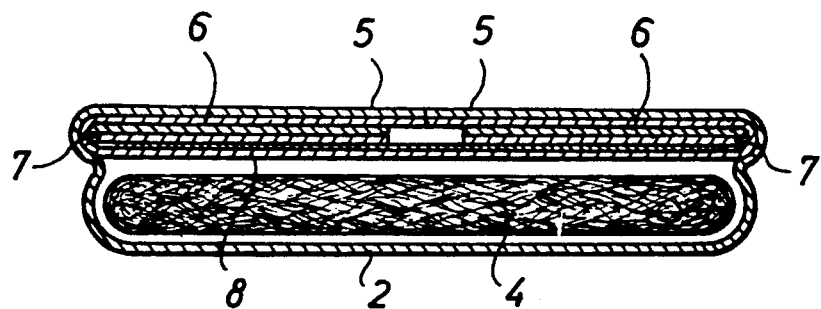
FIG. 1(b) is an enlarged sectional view showing the bent state of a pair of fixing elements thereof in the width direction (including the wing-like portions).
Figure 2:
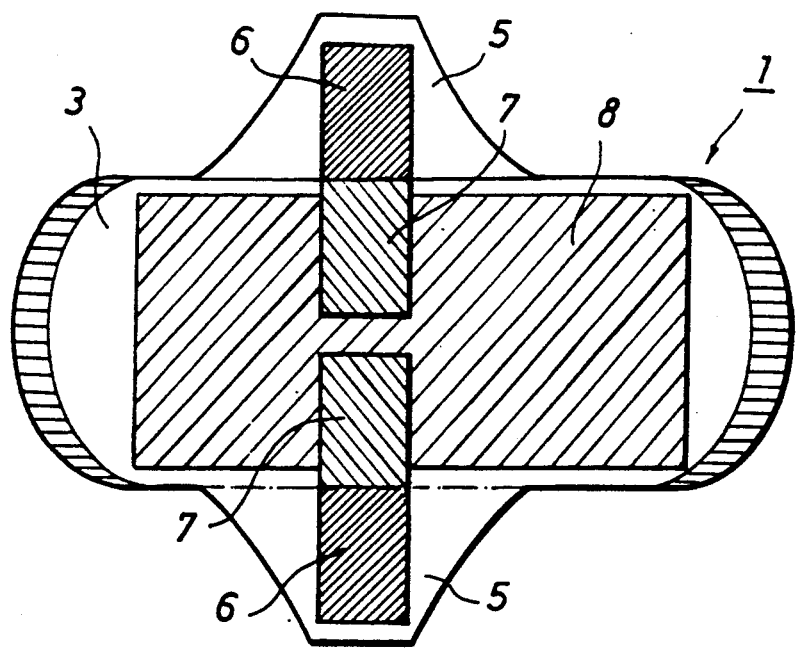
FIG. 2 is a plan view showing a spread state of the fixing elements of the catamenial napkin according to the first embodiment.

A catamenial napkin 1 of the first embodiment, as shown in FIGS. 1(a), 1(b) and 2, has a liquid permeable outer surface material (topsheet) 2, a liquid impermeable antileakage material (antileakage sheet) 3, a liquid retentive absorbent element 4 interposed between the sheets 2 and 3, and is formed in a generally vertically elongated shape.

One parts of the topsheet 2 and the antileakage sheet 3 extend outward in the width direction at both longitudinal side edges of the catamenial napkin 1 in such a manner to exhibit a generally trapezoidal shape, to thereby form a pair of wing-like fixing elements 5, 5, which are integral with a body of the catamenial napkin 1. The pair of fixing elements 5, 5 are located in a position slightly one-sided in the forward direction at both longitudinal side edges of the catamenial napkin 1 respectively, and a crotch portion is wrapped up between the fixing elements 5, 5 and the back side of the catamenial napkin 1 to thereby fix the catamenial napkin 1 to the shorts.

An outer surface of the antileakage sheet 3 forming the back sides of the respective fixing elements 5, 5 is provided with first adhesive portions 6, 6 respectively, and the antileakage sheet 3 is also provided at portions thereof opposed by the first adhesive portions 6, 6 in a state where the respective fixing elements 5, 5 are bent toward the back side of the body of the catamenial napkin 1 with second adhesive portions 7, 7 opposite to the first adhesive portions 6, 6 (see FIG. 2), the catamenial napkin 1 being surely fixed to the shorts by these two pairs of first and second adhesive portions 6 and 7. Adhesives used in the first and second adhesive portions 6 and 7 are of the type having a weak adhesive strength which requires no release paper. The arrangement is such that the first and second adhesive portions 6 and 7 are firmly adhered to each other and not separated easily. One example of such adhesive is disclosed in Japanese Utility Model Early Laid-open Publication No. Sho 59-153304. Each of the adhesive portions 6 and 7 is provided on the antileakage sheet 3 side with an adhesive having a strong adhesive strength forming a lower layer, and an adhesive having a weak adhesive strength applied on the lower layer to form an upper layer, thereby forming a two-layer structure. By forming the adhesive portions 6 and 7 in such a two-layer structure, the adhesive portions 6 and 7 can firmly be adhered to the antileakage sheet 3. On the other hand, the opposing adhesive portions 6 and 7 are adhered to each other with less amount of adhesive strength on the upper layer, so that the mutually adhered adhesive portions 6 and 7 can easily be separated without using release paper. As a result, the adhesive portions 6 and 7 can be adhered and separated with respect to each other. The strong adhesive is preferably of, for example, an acrylic series or rubber series, while the weak adhesive is preferably of, for example, an acrylic series. The adhesive strength of these adhesives can be adjusted properly by a well known method in the art.

In the catamenial napkin 1 of this embodiment, an antislip portion 8 is formed over the generally entire surface of the antileakage sheet 3. The antislip portion 8 can be formed by applying, for example, a polymer having a glass transition temperature Tg of 0° C. or less and foamed expandable polymer beads which are described in Japanese Patent Early Laid-open Publication No. Sho 63-73959.

The outer sheet 2, antileakage sheet 3 and absorbent element 4 are preferably formed of known materials which have been conventionally normally used.

Next, the mode of use of the catamenial napkin 1 according to the first embodiment will be described.

First, after each of the fixing elements 5, 5 is separated from the body of the catamenial napkin 1 which is in the state as shown in FIG. 1 and the catamenial napkin 1 is transformed into the state as shown in FIG. 2 where the fixing elements 5, 5 are spread outward, the rear surface of this catamenial napkin 1 is brought into contact with the back side of the crotch portion of the shorts and the catamenial napkin 1 is fixed to the crotch portion through the second adhesive portions 7, 7. Then, when the pair of fixing elements 5, 5 are bent inwardly to wrap up the both side edges of the crotch portion, the adhesive portions 6, 6 of fixing elements 5, 5 are adhered to the outer surface of the crotch portion thereby fixing the catamenial napkin 1 to the crotch portion. If the shorts with the catamenial napkin 1 adhered thereto in the manner as just mentioned are worn by a wearer, the catamenial napkin 1, holds the state where the catamenial napkin 1 is fixed by the fixing elements while it is deformed in accordance with the configuration of the wearer's crotch portion and intimately attached to the crotch portion.

Therefore, according to the first embodiment, the first adhesive portions 6, 6 are merely adhered to the second adhesive portions 7, 7 in the respective fixing elements 5, 5. Accordingly, when the catamenial napkin 1 is worn, the respective fixing elements 5, 5 are easily spread and pulled out from both side edge portions of the crotch portion of the shorts, the catamenial napkin 1 is adhered to the inner surface of the crotch portion through the second adhesive portions 7, 7 and then the catamenial napkin 1 is fixed to the crotch portion in the state where the fixing elements 5, 5 are adhered to the outer surface of the crotch portion through the adhesive portions 6, 6. Accordingly, the fixing operation is very convenient and no fixing error will occur. Further, while the shorts are worn, together with the function of the antislip portion 8, the catamenial napkin 1 can be surely fixed to the crotch portion through the two pairs of first and second adhesive portions 6 and 7. As a result, the catamenial napkin 1 is not displaced and is held stable in its initially fixed state. Even if the shape of the crotch portion is greatly changed due to the wearer's physical activity or movements, the catamenial napkin 1 follows the change in shape while maintaining its state where the catamenial napkin 1 is secured to the crotch portion, thus preventing the catamenial napkin 1 from being twisted. As a result, there is no fear that the shorts and the inner crotch portion will be stained with blood.

Furthermore, according to the first embodiment, since the first and second adhesive portions 6 and 7 can be contacted with and release from each other, no separate paper need be disposed between the adhesive portions 6 and 7. As a result, expensive release paper can be saved and manufacturing cost reduced therefore, an economical catamenial napkin 1 is obtained.

It should be understood that in the catamenial napkin shown in FIG. 2, an embodiment having no antislip portion 8 is also included within the score of the present invention.

The absorbent article of the present invention can be constructed in the form of catamenial napkins 1 according to second through seventh embodiments which are shown in FIGS. 3 through 10, respectively.

Figure 3:
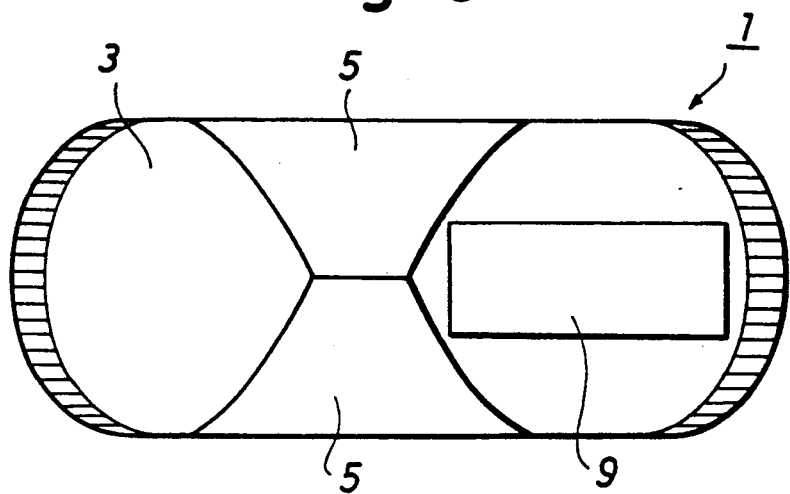
FIG. 3 is a view showing a catamenial napkin as a second embodiment of an absorbent article of the present invention.
Figure 4:
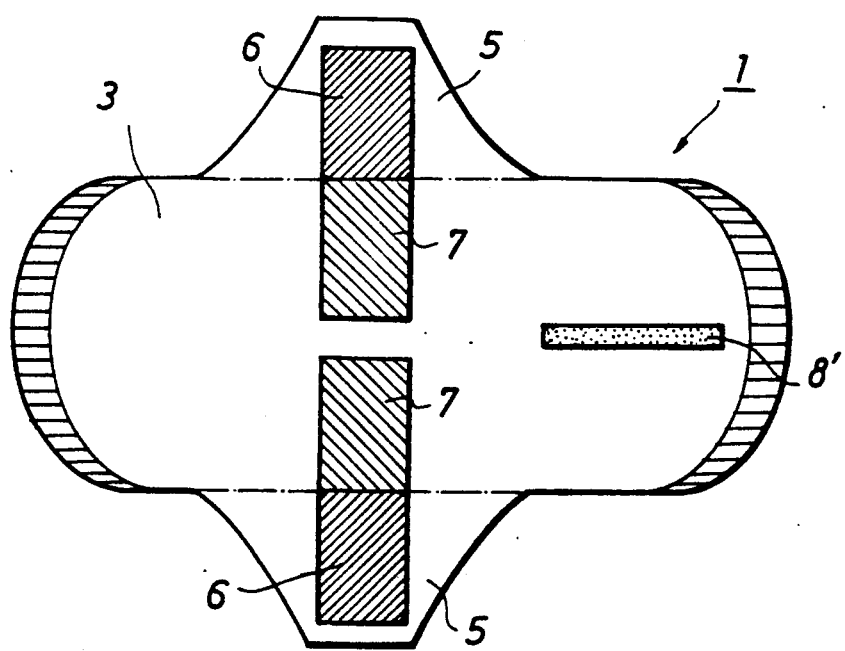
FIG. 4 is a view, corresponding to FIG. 2, of the second embodiment shown in FIG. 3.

The catamenial napkin 1 according to the second embodiment shown in FIGS. 3 and 4 is constructed in the same manner as that of the above-mentioned first embodiment, except that instead of the antislip portion 8 disposed to the entire surface of the antileakage sheet 3 in the catamenial napkin 1, an adhesive is applied to a generally central portion of a rear part of the antileakage sheet 3 in the longitudinal direction to form a third adhesive portion 8' and a release paper 9 is attached to the adhesive portion 8'. In this second embodiment, the adhesive portion 8' corresponds to the antislip portion 8 of the first embodiment. As a result, there can be expected the same operation and effect as the first embodiment except that it requires time and labor for removing the release paper 9 when the catamenial napkin 1 is worn. It may be designed such that the third adhesive portion 8' does not require a release paper as in the first embodiment.

Figure 5:
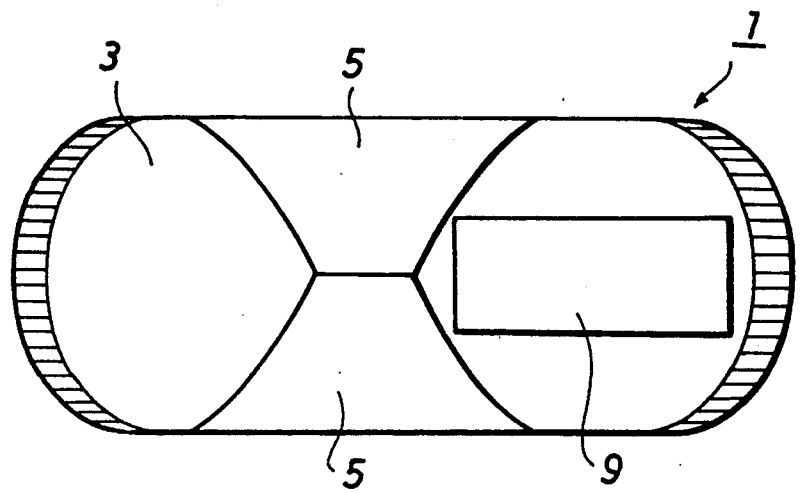
FIG. 5 is a view showing a catamenial napkin as a third embodiment of an absorbent article of the present invention.
Figure 6:
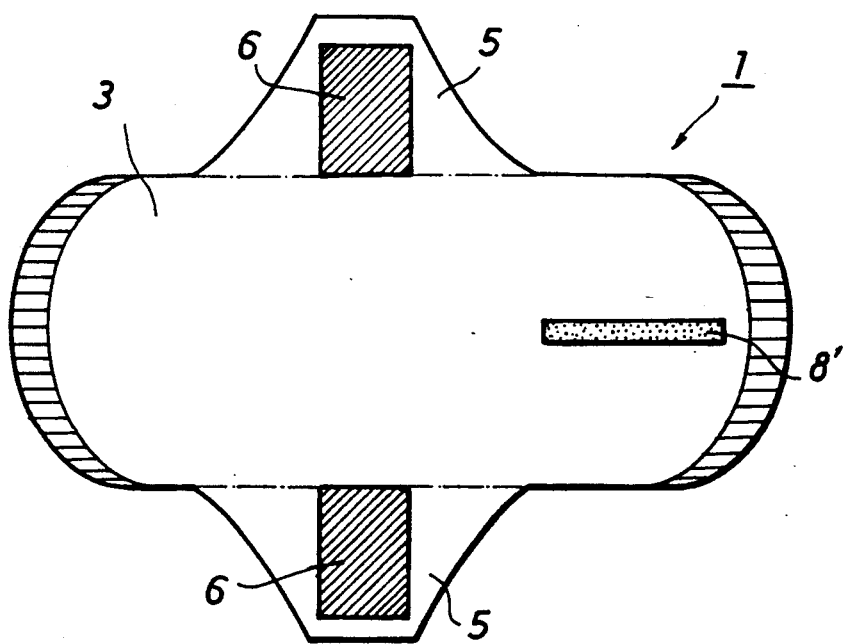
FIG. 6 is a view, corresponding to FIG. 2, of the third embodiment shown in FIG. 5.

Similarly, a catamenial napkin 1 according to the third embodiment shown in FIGS. 5 and 6 is constructed in the same manner as the catamenial napkin 1 according to the second embodiment shown in FIGS. 3 and 4 except that the adhesive portions 7, 7 of the body of the catamenial napkin 1 shown in FIGS. 3 and 4 are omitted as is apparent from FIGS. 5 and 6. Although the adhesive portions 6, 6 are designed such that they can be contacted with and separated from the antileakage sheet 3 in this embodiment, it is preferable to apply a separation treatment to the outer surface of the antileakage sheet 3 in order to enhance the ability of contact and separation of adhesive portions 6, 6 to and from antileakage sheet 3, respectively. Therefore, according to the third embodiment, there can be expected the similar operation and function as in the catamenial napkin 1 according to the second embodiment shown in FIGS. 3 and 4.

Figure 7A:
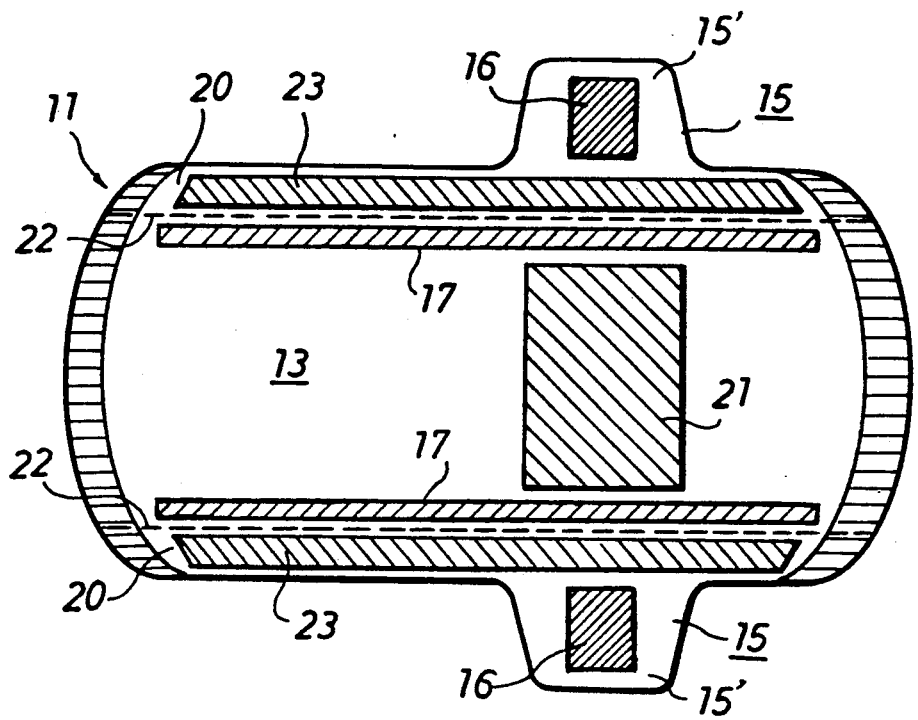
FIG. 7(a) is a view, corresponding to FIG. 2, showing a back side of a fourth embodiment of the present invention
Figure 7B:
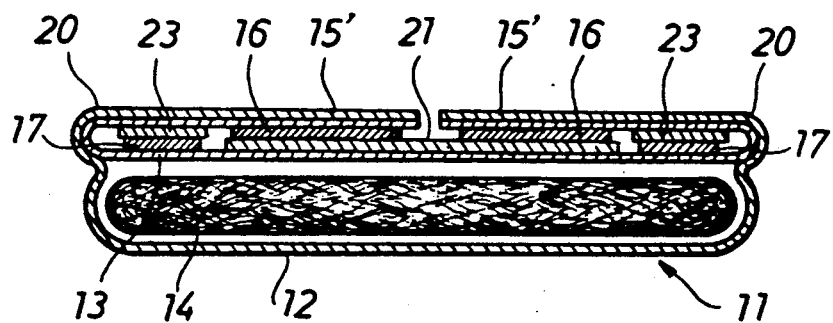
FIG. 7(b) is an enlarged sectional view showing the bent states of the fixing elements thereof in the width direction (including wing-like portions)

Likewise, the catamenial napkin 11 according to the fourth embodiment shown in FIGS. 7(a)–7(b) includes an outer surface 12 and an antileakage sheet 13 forming a pair of wing-like fixing elements 15, 15 having a pair of flap portions 20, 20 extending outwardly in the width direction over the entire length thereof at the both side edge portions as apparent from FIG. 7(a). That is, the fixing elements 15, 15 are formed in a wing shape because one part of the respective flaps 20, 20 extends outwardly in the width direction at a slightly forward part in the longitudinal direction in such a manner as to exhibit a generally trapezoidal configuration.

Further, the wing-like portions 15', 15' of the antileakage sheet 13 forming the back sides of the fixing elements 15, 15 are provided with the first adhesive portions 16, 16 respectively, and the catamenial napkin 11 is provided with a rectangular-shaped first separation treatment portion 21 formed at a slightly forward part of the center of the body thereof in such a manner as to correspond to the first adhesive portions 16, 16.

Further, the pair of flap portions 20, 20 are provided with folds 22, 22 formed thereon over the entire length of inner side edges thereof, and the respective flap portions 20, 20 are folded inwardly in the width direction along the respective folds 22, 22 so as to be overlapped with the rear surface of the catamenial napkin 11. Moreover, the flap portions 20, 20 are provided with elongated second adhesive portions 17, 17 formed thereon at inner sides of the respective folds 22, 22 along generally the entire length of the folds 22, 22, and with second separation treatment portions 23, 23 formed thereon at external sides of the respective folds 22, 22 over the entire area excepting the wing-like portion 15', 15'.

In the catamenial napkin 11 according to the fourth embodiment, when the napkin 11 is not in use, the pair of flap portions 20, 20 respectively are folded inward in the width direction along the folds 22, 22, so that the pair of fixing elements 15, 15 are separably overlapped with the first separation treatment portions 21, 21 of the body of the catamenial napkin 11 through the first adhesive portions 16, 16, respectively and the respective flap portions 20, 20 are separably overlapped with the second adhesive portions 17, 17 on both side portions of the body of the catamenial napkin 11.

On the other hand, when the catamenial napkin 11 is in use, the flap portions 20, 20 of the respective fixing elements 15, 15 are spread and the back sides thereof are contacted with the inner surface of the crotch portion of the shorts. Then, the fixing elements 15, 15 are fixed to the crotch portion through the second adhesive portions 17, 17 on both sides of the body of the catamenial napkin 11. Then, the respective flap portions 20, 20 are bent along the folds 22, 22 so as to be overlapped with the outer surface of the crotch portion. As a result, they are more surely secured to the crotch portion through the first adhesive portions 16, 16 of the respective wing-like portions 15', 15'. Accordingly, the catamenial napkin according to the fourth embodiment can be more surely secured to the crotch portion compared with those of the first through third embodiments.

Figure 7C:
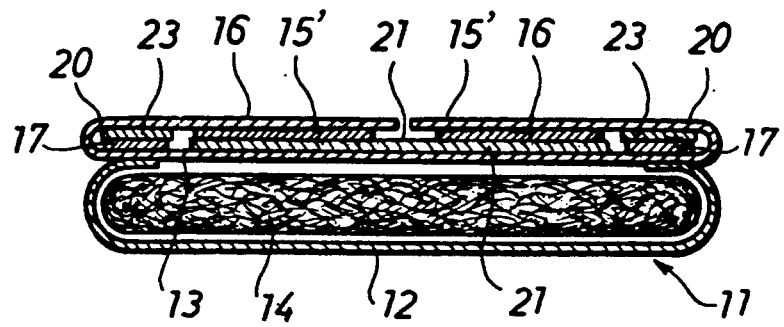
FIG. 7(c) is a view, corresponding to FIG. 7(b), of a partly modified embodiment of the fourth embodiment.
Figure 8:
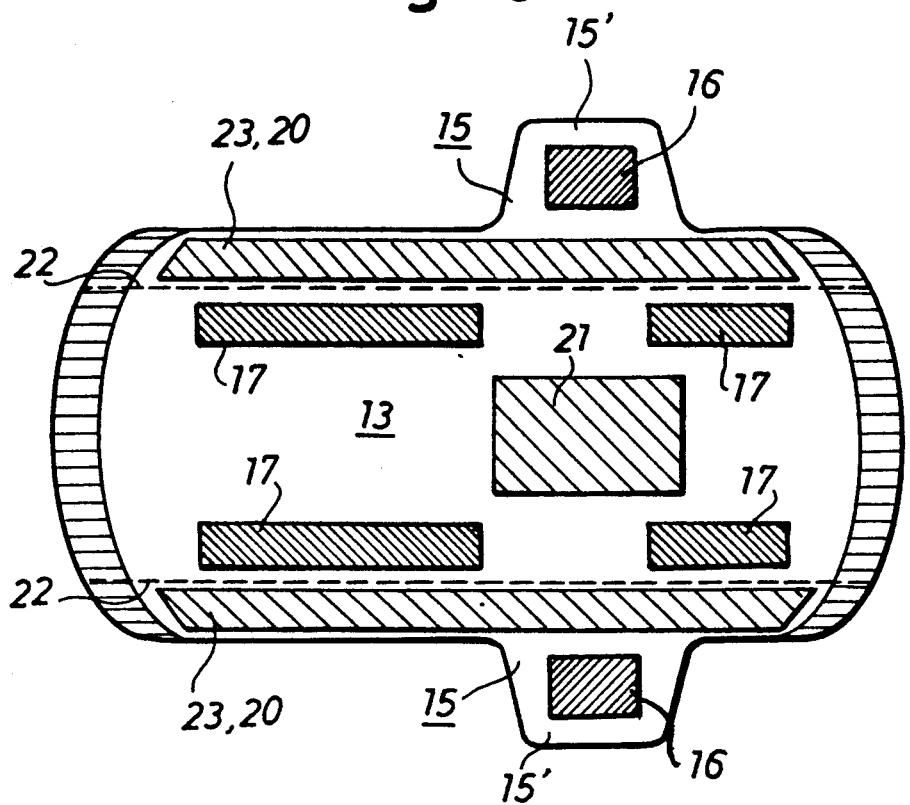
FIG. 8 is a view showing a catamenial napkin as a fifth embodiment of an absorbent article of the present invention.

Furthermore, a catamenial napkin 11 according to the fifth embodiment shown in FIG. 8 is basically constructed in the same manner as the catamenial napkin according to the fourth embodiment shown in FIG. 7(a) excepting the mode for forming the second adhesive portions 17, 17. That is, in the catamenial napkin 11 according to the fifth embodiment, the pair of second adhesive portions 17, 17 are divided into a front part and a rear part on the body of the catamenial napkin 11 respectively, and the width of second adhesive portion 17, 17 are slightly wider than those shown in FIG. 7. As a result, the dimension of the second separation treatment portion 23 formed on the rear surface of the body of the catamenial napkin 11 is slightly enlarged. Accordingly, the same operation and function of the fourth embodiment shown in FIG. 7(a) can be expected in the fifth embodiment, too.

Figure 9A:
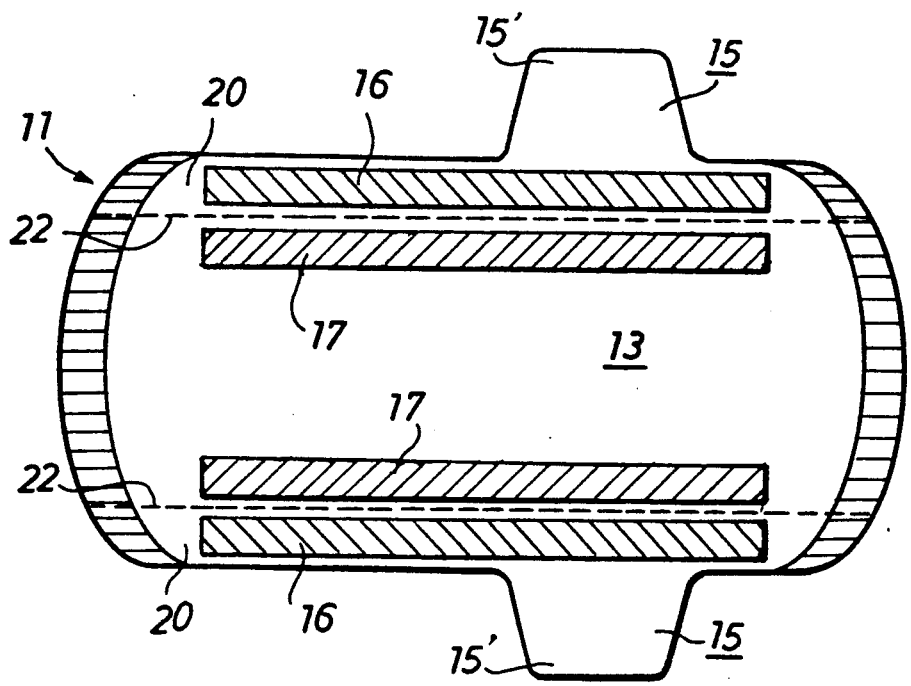
FIG. 9(a) is a view showing a back side of a sixth embodiment of the present invention.
Figure 9B:
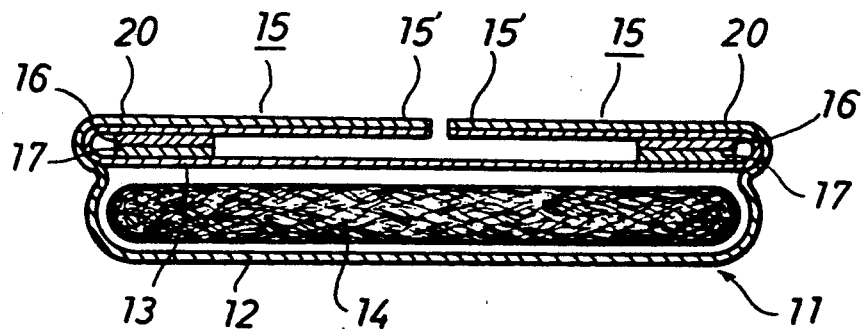
FIG. 9(b) is a view corresponding to FIG. 7(b)

Further, in a catamenial napkin 11 according to the sixth embodiment shown in FIGS. 9(a) and 9(b), the fixing elements 15, 15 are provided with the wing-like portions 15', 15', the flap portions 20, 20, and the folds 22, 22 as shown in FIGS. 7(a) and 8(b). The fixing elements 15, 15 are provided on both sides of the respective folds 22, 22 with the first adhesive portions 16, 16 and the second adhesive portions 17, 17 as in the respective embodiments shown in FIGS. 1 through 6. That is, the first adhesive portions 16, 16 are formed in elongated shapes on the flap portions 20, 20 respectively, while the second adhesive portions 17, 17 are formed in elongated shapes on both sides of the body of the catamenial napkin 11 respectively.

Figure 10:
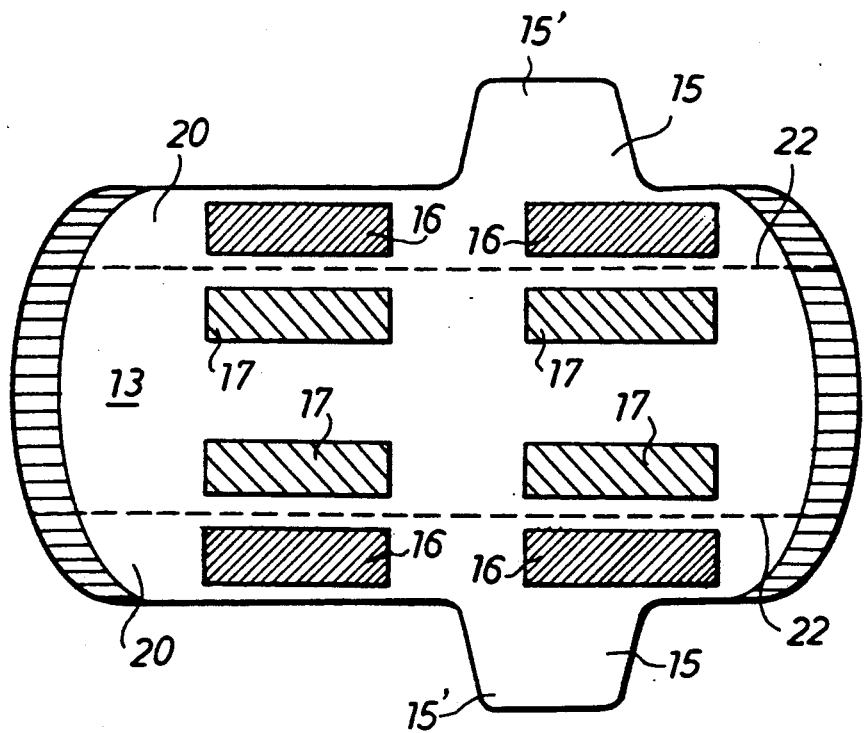
FIG. 10 is a view, corresponding to FIG. 9(a), showing a catamenial napkin as a seventh embodiment of an absorbent article of the present invention.

Furthermore, a catamenial napkin 11 according to the seventh embodiment shown in FIG. 10 is formed in the same manner as that shown in FIG. 9, except that the first and second adhesive portions 16, 16 and 17, 17 are divided into a front part and a rear part, respectively and the widths thereof are wider than those of FIG. 9.

Accordingly, a catamenial napkin 11 according to the sixth and seventh embodiments shown in FIGS. 9 and 10 is more surely secured to the crotch portion than in the first through third embodiments shown in FIGS. 1 through 6, and there can be expected the same operation and effect as those of the first through third embodiments.

Figure 9C:
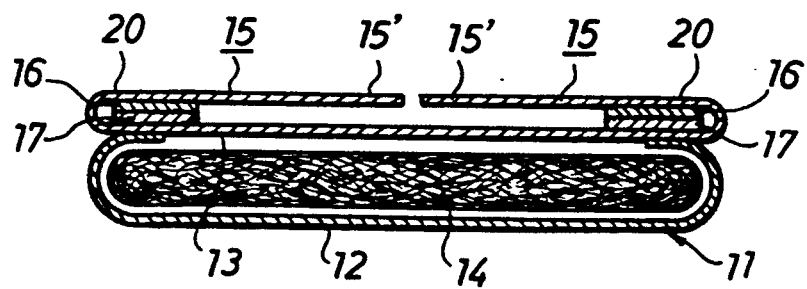

The absorbent article of the present invention is, by no means, limited to the fixing elements of the above-mentioned embodiments as long as it includes a pair of fixing elements extending outwardly in a width direction from both longitudinal edges of the absorbent article, each of the fixing elements is provided on at least a back side thereof with a first adhesive portion having no release paper; and the pair of fixing elements are able to be adhered to and separated from a back side of the absorbent article through the first adhesive portions. For example, the fixing elements can be formed not only in such a manner as to overlap the outer material 2 and the antileakage material 3 as shown in FIGS. 1(b), 7(b), and 9(b), but also to extend only the antileakage material 3 as shown in FIGS. 7(c) and 9(c). Moreover, they may be formed of an independent member from the outer material 2 or the antileakage material 3. Like this, they can be modified in various ways.

Furthermore, an absorbent article of the present invention is likewise applicable to an absorbent article such as incontinent pad, catamenial pad, etc. besides the catamenial napkin as mentioned in the above-mentioned embodiments.

What is claimed is:

1. An absorbent article having a body with generally elongated sides, comprising:

a liquid permeable outer material top layer to be located next to a wearer's body;

a liquid impermeable antileakage material bottom layer;

a liquid retentive absorbent element interposed between said top and said bottom layer;

said bottom layer having a front side in contact with said liquid retentive absorbent element and a back side to be located next to a pair of shorts about said wearer's body;

at least said bottom layer extending beyond a periphery defined by said elongated sides of the body so as to form a pair of fixing elements;

said fixing elements being provided with first adhesive portions on said back side of the bottom layer making up said fixing elements, such that when said fixing elements are folded so as to remain within said periphery defined by the elongated sides of the body, said first adhesive portions are sandwiched between said fixing elements and a portion of said bottom layer within said periphery defined by the elongated sides of the body;

said first adhesive portions being non-separably adhered to said fixing elements and separably adhered to said portion of said bottom layer within said periphery defined by the elongated sides of the body;

said first adhesive portion requiring no release paper; and second adhesive portions, provided on said portion of the bottom layer within said periphery defined by the elongated sides of the body, and opposite to said first adhesive portions, said second adhesive portions are separably adhered to said first adhesive portions without a release paper.

2. An absorbent article having a body with generally elongated sides, comprising:

a liquid permeable outer material top layer to be located next to a wearer's body;

a liquid impermeable antileakage material bottom layer, at least one of said bottom layer and said top layer extending beyond a periphery defined by the elongated sides of the body to form a pair of fixing elements;

a liquid retentive absorbent element interposed between said top and said bottom layer;

said bottom layer having a front side in contact with said liquid retentive absorbent element and a back side to be located next to a pair of shorts about said wearer's body;

said fixing elements being provided with first adhesive portions on said back side of the bottom layer making up said fixing elements, such that when said fixing elements are folded so as to remain within said periphery defined by the elongated sides of the body, said first adhesive portions are sandwiched between said fixing elements and a portion of said bottom layer within said periphery defined by the elongated sides of the body;

said first adhesive portions being non-separably adhered to said fixing elements and separably adhered to said portion of said bottom layer within said periphery defined by the elongated sides of the body;

said first adhesive portion requiring no release paper; and second adhesive portions, provided on said portion of the bottom layer within said periphery defined by the elongated sides of the body, and opposite to said first adhesive portions, said second adhesive portions are separably adhered to said first adhesive portions without a release paper.

3. An absorbent article having a body with generally elongated sides, comprising:

a liquid permeable outer material top layer to be located next to a wearer's body;

a liquid impermeable antileakage material bottom layer;

a liquid retentive absorbent element interposed between said top and said bottom layer;

said bottom layer having a front side in contact with said liquid retentive absorbent element and a back side to be located next to a pair of shorts about said wearer's body;

at least said bottom layer extending beyond a periphery defined by said elongated sides of the body so as to form a pair of fixing elements, said fixing elements being formed along substantially an entire length of each of said elongated sides of the body;

said fixing elements being provided with first adhesive portions on said back side of the bottom layer making up said fixing elements, such that when said fixing elements are folded so as to remain within said periphery defined by the elongated sides of the body, said first adhesive portions are sandwiched between said fixing elements and a portion of said bottom layer within said periphery defined by the elongated sides of the body;

said first adhesive portions being non-separably adhered to said fixing elements and separably adhered to said portion of said bottom layer within said periphery defined by the elongated sides of the body;

said first adhesive portion requiring no release paper; and second adhesive portions, provided on said portion of the bottom layer within said periphery defined by the elongated sides of the body, and opposite to said first adhesive portions, said second adhesive portions are separably adhered to said first adhesive portions.

4. An absorbent article having a body with generally elongated sides, comprising:

a liquid permeable outer material top layer to be located next to a wearer's body;

a liquid impermeable antileakage material bottom layer;

a liquid retentive absorbent element interposed between said top and said bottom layer;

said bottom layer having a front side in contact with said liquid retentive absorbent element and a back side to be located next to a pair of shorts about said wearer's body;

said bottom and said top layer extending beyond a periphery defined by said elongated sides of the body so as to form a pair of fixing elements, said fixing elements being formed along substantially an entire length of each of said elongated sides of the body;

said fixing elements being provided with first adhesive portions on said back side of the bottom layer making up said fixing elements, such that when said fixing elements are folded so as to remain within said periphery defined by the elongated sides of the body, said first adhesive portions are sandwiched between said fixing elements and a portion of said bottom layer within said periphery defined by the elongated sides of the body;

said first adhesive portions being non-separably adhered to said fixing elements and separably adhered to said portion of said bottom layer within said periphery defined by the elongated sides of the body;

said first adhesive portion requiring no release paper; and second adhesive portions, provided on said portion of the bottom layer within said periphery defined by the elongated sides of the body, and opposite to said first adhesive portions, said second adhesive portions are separably adhered to said first adhesive portions.

* * * * *